(12) United States Patent
Oguchi et al.

(10) Patent No.: US 6,759,540 B2
(45) Date of Patent: Jul. 6, 2004

(54) CRYSTALLINE MWW-TYPE TITANOSILICATE CATALYST FOR PRODUCING OXIDIZED COMPOUND, PRODUCTION PROCESS FOR THE CATALYST, AND PROCESS FOR PRODUCING OXIDIZED COMPOUND BY USING THE CATALYST

(75) Inventors: Wataru Oguchi, Oita (JP); Katsuyuki Tsuji, Kawasaki (JP); Takashi Tatsumi, Kawasaki (JP); Peng Wu, Yokohama (JP)

(73) Assignee: Showa Denko K.K., Tokyo (JP)

( * ) Notice: Subject to any disclaimer, the term of this patent is extended or adjusted under 35 U.S.C. 154(b) by 51 days.

(21) Appl. No.: 09/959,937

(22) PCT Filed: Sep. 27, 2001

(86) PCT No.: PCT/JP01/08469

§ 371 (c)(1),
(2), (4) Date: Nov. 13, 2001

(87) PCT Pub. No.: WO02/28774

PCT Pub. Date: Apr. 11, 2002

(65) Prior Publication Data

US 2003/0040649 A1 Feb. 27, 2003

Related U.S. Application Data

(60) Provisional application No. 60/247,963, filed on Nov. 14, 2000.

(30) Foreign Application Priority Data

Sep. 29, 2000 (JP) ........................................ 2000-298133

(51) Int. Cl.$^7$ ...................... C07D 301/12; C07D 301/19
(52) U.S. Cl. ...................... 549/529; 549/531; 502/107; 502/242
(58) Field of Search ................................. 549/529, 531; 502/107, 242

(56) References Cited

U.S. PATENT DOCUMENTS 5,919,430 A * 7/1999 Hasenzahl et al. .......... 423/702
6,114,551 A    9/2000 Levin et al.

OTHER PUBLICATIONS

International Search Report for PCT/JP01/08469 dated Jul. 17, 2002.
Peng Wu et al, "Hydrothermal Synthesis of a Novel titanosilicate with MWW Topology", Chemistry Letter, No. 7, pp. 774–775 (Jul. 2000).
Peng Wu et al, A Novel Titanosilicate with MWW Structure. I. Hydrothermal Synthesis, Elimination of Extraframework titanium, and Characterizations, J. Phys. Chem. B 2001, vol. 105, No. 15, pp. 2897–2905 (Apr. 2001).

* cited by examiner

*Primary Examiner*—Ba K. Trinh
(74) *Attorney, Agent, or Firm*—Sughrue Mion, PLLC

(57) ABSTRACT

A crystalline titanosilicate catalyst which is usable as a catalyst in the oxidation reaction of a compound having a carbon-carbon double bond and at least one other functional group, a process for producing the catalyst, and a process for producing an oxidized compound by an oxidation reaction using the catalyst. It has been found that a crystalline titanosilicate having a structural code of MWW effectively functions as a catalyst in an oxidation reaction of a compound having a carbon-carbon double bond and at least one other functional group wherein the carbon-carbon double bond of the compound is oxidized by using a peroxide as an oxidizing agent, thereby to highly selectively provide an intended oxidized compound.

11 Claims, No Drawings

CRYSTALLINE MWW-TYPE TITANOSILICATE CATALYST FOR PRODUCING OXIDIZED COMPOUND, PRODUCTION PROCESS FOR THE CATALYST, AND PROCESS FOR PRODUCING OXIDIZED COMPOUND BY USING THE CATALYST

This application in a 371 of PCT/JP01/08469 filed on Aug. 27, 2000.

This application claims the benefit of an application based on U.S. Provisional Application Ser. No. 60/247,963 (filed on Nov. 14, 2000).

TECHNICAL FIELD

The present invention relates to a crystalline titanosilicate catalyst having a structural (or framework type) code of MWW, which is usable as a catalyst in an oxidation reaction of the carbon-carbon double bond of a compound having a carbon-carbon double bond and at least one other functional group. The present invention also relates to a process for producing such a catalyst and a process for producing an oxidized compound using this catalyst.

More specifically, the present invention relates to a crystalline titanosilicate catalyst having a structural code of MWW, which is usable as a catalyst in an oxidation reaction of the carbon-carbon double bond of a compound having a carbon-carbon double bond and at least one other functional group using a peroxide as an oxidizing agent; a process for producing such a catalyst; and a process for producing an oxidized compound (particularly, an epoxy compound) comprising performing an oxidation reaction of the carbon-carbon double bond of a compound having a carbon-carbon double bond and at least one other functional group in the presence of the catalyst.

BACKGROUND ART

In general, "zeolite" is a generic term for crystalline and porous aluminosilicates for, and the basic unit of the structure of a zeolite is $(SiO_4)^{4-}$ or $(AlO_4)^{5-}$ having a tetrahedral structure. However, it has recently been clarified that a structure peculiar to or analogous to such a zeolite is also present in many other oxides such as aluminophosphate.

In addition, according to the International Zeolite Association (hereinafter, simply referred to as "IZA") who defines the zeolite in W. Meier, D. H. Meier, D. H. Olxon and Ch. Baerlocher, *Atlas of Zeolite Structure Types*, 4th Edition, Elsevier (1996) (hereinafter, simply referred to as "Atlas"), substances having the same structure, other than aluminosilicate, are described as an object substance in prescribing the structure, and these substances are called "zeolite-like materials" in the Atlas.

The history of this definition is described in detail in Yoshio Ono and Takeaki Yajima, *Zeolite no Kagaku to Kogaku* (*Science and Engineering of Zeolites*), pp. 1–2, published by Kodansha (Jul. 10, 2000).

In the present specification, the definition of "zeolite" follows the above definition as described in Yoshio Ono and Takeaki Yajima, *Zeolite no Kagaku to Kogaku* (*Science and Engineering of Zeolite*), published by Kodansha (Jul. 10, 2000), where the term "zeolite" may include not only aluminosilicates but also substances (such as titanosilicate) having a structure analogous to aluminosilicate.

In the present specification, the structures of zeolite and zeolite-like materials are denoted by a structural code, using three alphabetic capital letters, approved by IZA and originated in the standard substance which had first been used for the clarification of the structure thereof. The structural codes includes those contained in Atlas and those approved in the 4th edition, et seq.

In the present specification, the terms "aluminosilicate" and "titanosilicate" are not limited at all by the properties and/or states thereof (such as crystalline or amorphous, or porous or not porous). Therefore, in the present specification, these terms denote "aluminosilicates" and "titanosilicates" of all properties, unless specifically indicated otherwise.

In the present specification, the term "molecular sieve" means an activity or operation for classifying molecules by the size thereof, and the term also means a substance having such a function. zeolite is also included in the definition of a molecular sieve. The details thereon are described in the portion relating to "molecular sieve" in *Hyojun Kagaku Yogo Jiten* (*Standard Chemical Glossary*), edited by the Chemical Society of Japan, published by Maruzen (Mar. 30, 1991).

In recent years, various studies have been made on the oxidation reactions of organic compounds by using a titanosilicate which is a zeolite, as a catalyst, and using a peroxide as an oxidizing agent. Among these, a catalyst named "TS-1", which is a crystalline titanosilicate, has been found to show an activity in an oxidation reaction using various peroxides, after the process for synthesizing the same was disclosed in U.S. Pat. No. 4,410,501, and TS-1 has been applied to various reactions. Specific examples thereof include the method disclosed in JP-B-4-5028 ("JP-B" as used herein means an "examined Japanese Patent publication"), where TS-1 is used as a catalyst in the epoxidation of an olefin compound using hydrogen peroxide or an organic peroxide as an oxidizing agent.

The structural code of the titanosilicate TS-1 is "MFI", which is the same code as the structural code of a representative synthetic zeolite ZSM-5, and TS-1 contains a ring structure containing ten (10) oxygen atoms (as described in Yoshio Ono and Takeaki Yajima, *Zeolite no Kagaku to Kogaku*, p. 4, published by Kodansha). As TS-1 has a relatively small pore size of 0.51 nm to 0.56 nm in terms of a calculated value therefor, the scope of olefin compounds which can be epoxidized by using TS-1 is limited. Further, both of the rate of the diffusion of an olefin compound as a reaction starting material into the inside of a pore and the rate of the effusion of an epoxy compound as a reaction product from the pore are low, so that a reaction activity which is sufficiently high, in view of the industrial use of TS-1, cannot be achieved in many cases. Furthermore, there is a problem such that a ring-opening reaction of the epoxy group of an epoxy compound as a reaction product is liable to occur, and the resultant selectivity is disadvantageously decreased.

On the other hand, JP-A-7-242649 ("JP-A" as used herein means "unexamined Japanese Patent publication") discloses a method of performing an epoxidation reaction of an olefin compound by using a crystalline titanium-containing molecular sieve having a structure similar to aluminum-free zeolite Beta (structural code: *BEA) as a catalyst and by using hydrogen peroxide or an organic peroxide as an oxidizing agent.

Since the *BEA has a large pore diameter as compared with that of the structural code of MFI for the titanosilicate TS-1, an effect of enabling a reaction of a sterically bulky compound or an effect of elevating the diffusion rate to thereby improve the resultant reaction rate was expected. In some examples of the above-mentioned Patent publication, a compound which does not react even in the case using the titanosilicate TS-1 can be actually oxidized. However, there are caused problems that the conversion of an oxidizing agent is low when hydrogen peroxide is used as the oxidizing agent for the epoxidation reaction, and that a ring-opening reaction of the epoxide is caused to produce a corresponding glycol, and as a result, the resultant selectivity is decreased. Further, in the case of the molecular sieve as described in this Patent publication, the decreasing rate of activity is rather high. That is, the catalyst life is short, and therefore it is necessary to repeat the regeneration of the catalyst frequently, whereby this point seriously hinders the implementation of such a molecular sieve on an industrial scale.

On the other hand, in recent years, synthetic zeolites having a structural code of MWW, which is different from those of MFI or *BEA, are attracting attention. The process for producing the same is disclosed, for example, in JP-A-63-297210.

Further, according to Peng Wu, Takashi Tatsumi and Takayuki Komatsu, *Chemistry Letters*, 774 (2000), it has been reported that when a crystalline titanosilicate having the structural code of MWW and containing a titanium atom in the crystal structure thereof is produced, and cyclohexene is oxidized by using this crystalline titanosilicate as a catalyst and by using hydrogen peroxide, cyclohexene oxide can be produced.

However, the yield of the intended product is rather low, while both of the resultant epoxide and diol are produced in a considerably large amount, whereby a tendency of selectively providing any of these compounds is not observed. Therefore, there is a caused problem when this method is intended to be utilized industrially.

As described hereinabove, various proposals have been made for conducting the oxidation reaction of an olefin compound by using a titanosilicate as a catalyst and by using a peroxide as an oxidizing agent. However, industrially practicable techniques are rather limited, and further, in any of the above-mentioned cases, only an oxidation reaction of a simple compound having a carbon-carbon double bond is disclosed. There has not yet been reported a titanosilicate which is usable as a catalyst in the oxidation reaction of a compound not only having a carbon-carbon double bond and but also having at least one other functional group.

DISCLOSURE OF INVENTION

An object of the present invention is to provide a crystalline titanosilicate catalyst which is usable as a catalyst in a selective oxidation reaction of the carbon-carbon double bond of a compound having a carbon-carbon double bond and at least one other functional group.

Another object of the present invention is to provide a process for producing such a titanosilicate catalyst, and to provide a process for producing an oxidized compound by an oxidation reaction using the catalyst.

As a result of earnest study for solving the above-mentioned problems, the present inventors have found that a crystalline titanosilicate catalyst having a structural code of MWW can effectively function as a catalyst for a reaction wherein the carbon-carbon double bond of a compound having a carbon-carbon double bond and at least one other functional group is oxidized by using a peroxide, so as to provide an intended oxidized compound highly selectively. The present invention has been accomplished based on this discovery.

More specifically, the present invention, in an aspect, is a crystalline MWW-type titanosilicate catalyst, for producing an oxidized compound, which is usable in producing an oxidized compound by an oxidation reaction of a compound having a carbon-carbon double bond and at least one other functional group wherein the carbon-carbon double bond of the compound is oxidized by using a peroxide as an oxidizing agent. The catalyst has an MWW structure and is represented by the following (chemical) composition formula (1):

$xTiO_2 \cdot (1-x)SiO_2$            Composition formula (1)

(wherein x is a number of 0.0001 to 0.2).

The present invention, in a second aspect, is a crystalline MWW-type titanosilicate catalyst for producing an oxidized compound, which is usable in producing an oxidized compound by an oxidation reaction of a compound having a carbon-carbon double bond and at least one other functional group wherein the carbon-carbon double bond of the compound is oxidized by using a peroxide as an oxidizing agent. The catalyst has an MWW structure and is represented by the following composition formula (2):

$xTiO_2 \cdot yM_2O_3 \cdot (1-x-2y)SiO_2$            Composition formula (2)

(wherein M represents at least one element selected from the group consisting of aluminum, boron, chromium, gallium and iron, x is a number of 0.0001 to 0.2 and y is a number of 0.0001 to 0.1).

The present invention in a third aspect is a process for producing the crystalline MWW-type titanosilicate catalyst for producing an oxidized compound according to the present invention in the above-mentioned first or second aspect thereof.

The present invention in a fourth aspect is a process for producing an oxidized compound, comprising: performing an oxidation reaction of a compound having a carbon-carbon double bond and at least one other functional group wherein the carbon-carbon double bond of the compound is oxidized by using a peroxide as an oxidizing agent in the presence of the crystalline MWW-type titanosilicate catalyst for producing an oxidized compound according to the present invention in the first or second aspect.

Best Mode for Carrying Out the Invention

Hereinbelow, the present invention will be described in detail with reference to the accompanying drawings as desired. In the following description, "%" and "part(s)" representing a quantitative proportion or a ratio are based on mass, unless otherwise noted specifically.

At first, the present invention in the first aspect and the present invention in the second aspect will be described.

The present invention in the first aspect is a crystalline MWW-type titanosilicate catalyst for producing an oxidized compound, which is usable in producing an oxidized compound by an oxidation reaction of a compound having a carbon-carbon double bond and at least one other functional group wherein the carbon-carbon double bond of the compound is oxidized by using a peroxide as an oxidizing agent. The catalyst has an MWW structure and is represented by the following composition formula (1):

$xTiO_2 \cdot (1-x)SiO_2$            Composition formula (1)

(wherein x is a number of 0.0001 to 0.2).

The present invention in a second aspect is a crystalline MWW-type titanosilicate catalyst for producing an oxidized compound, which is usable in producing an oxidized compound by an oxidation reaction of a compound having a carbon-carbon double bond and at least one other functional group wherein the carbon-carbon double bond of the compound is oxidized by using a peroxide as an oxidizing agent. The catalyst has an MWW structure and is represented by the following composition formula (2):

$$xTiO_2 \cdot yM_2O_3 \cdot (1-x-2y)SiO_2 \quad \text{Composition formula (2)}$$

(wherein M represents at least one element selected from the group consisting of aluminum, boron, chromium, gallium and iron, x is a number of 0.0001 to 0.2 and y is a number of 0.0001 to 0.1).

In the crystalline MWW-type titanosilicate catalyst for producing an oxidized compound according to the present invention in the first aspect, the ratio of constituent units $TiO_2$ and $SiO_2$ present in the catalyst can be specified by the molar ratio therebetween. Therefore, "x" means the molar ratio of $TiO_2$ present in the titanosilicate, and (1−x) means the molar ratio of $SiO_2$ also present in the titanosilicate. In the other words, the ratio x/(1−x) merely shows the molar ratio of titanium/silicon, and this ratio does not exclude the presence of at least one other element in the above-mentioned crystalline MWW-type titanosilicate for producing an oxidized compound.

In the composition formula (1), the range of x is from 0.0001 to 0.2, preferably from 0.005 to 0.2, more preferably from 0.01 to 0.1. In addition to the titanium species which have been introduced into the framework by substituting with silicon, a titanium species may be present at a site outside the crystal framework (or skeleton). For example, a 6-coordination titanium species or an anatase-like titanium oxide may be present together with the above-mentioned titanium species. However, such a titanium species outside the framework generally has a tendency-such that it promotes a side reaction or narrows the pores in the titanosilicate so as to inhibit the diffusion of a substance relating to the reaction. Therefore, the titanium species present at a site outside the crystal framework, if present, may preferably be present in a smaller amount.

In general, the x specified in the composition formula (1) shows an estimated ratio of titanium contained within the framework. In practice, when titanium is present outside the framework in addition to titanium within the framework, it is difficult to precisely quantitate the titanium contained within the framework. In general, for example, in the ultraviolet-visible absorption spectrum of a titanosilicate, the absorption in the vicinity of 210 nm is assigned to titanium within the framework, the absorption in the vicinity of 260 nm is assigned to a 6-coordination titanium species outside the framework, and the absorption in the vicinity of 330 nm is assigned to an anatase-like titanium species. Therefore, if an absorption is present in the vicinity of 210 nm, this absorption reveals that the titanosilicate corresponding to the spectrum contains titanium within the framework. Actually, the titanosilicate catalyst according to the present invention in the first aspect has an absorption in the vicinity of 220 nm, and this absorption reveals the presence of titanium within the framework. However, when another absorption is present at other wavelengths, it is difficult to quantitatively discuss the ratio of these titanium species present in the titanosilicate, even in a case where other means such as nuclear magnetic resonance method or infrared absorption method is combined with the above ultraviolet-visible absorption spectrum.

Only one clear fact is that the value of the molar ratio of titanium to silicon calculated from the ratio between titanium and silicon determined by the component analysis such as elemental analysis, is the maximum value of the amount of titanium contained within the framework. As described above, it is difficult to directly determine the molar ratio of titanium contained within the framework. Therefore, in the present invention, the molar ratio of titanium to silicon calculated by the component analysis as x in the composition formula (1) is for convenience used as the molar ratio of titanium contained within the framework.

The crystalline titanosilicate catalyst according to the present invention in the first aspect having a structural code of MWW wherein silicon is partially substituted with titanium may contain an element other than titanium, silicon and oxygen, as long as such an element does not greatly cause an adverse effect on the reactivity of the catalyst. In a case where the catalyst according to the present invention in the first aspect is produced by a production process using boron as a structure supporting agent, as described hereinafter, a slight amount of boron may remain in the catalyst in many cases, even if an operation for removing boron is performed. However, boron in a small amount does not have any serious effect on the reactivity of the catalyst, and therefore, boron can be present in the catalyst in a substantial amount. In principle, other trivalent metals such as aluminum, gallium, iron and chromium may also be used as a structure supporting agent in place of boron, and in such a case, these elements may sometimes remain within and outside the framework.

In this case, there is formed a crystalline MWW-type titanosilicate catalyst for producing an oxidized compound according to the present invention in the second aspect. That is, the present invention in the second aspect is a crystalline MWW-type titanosilicate catalyst for producing an oxidized compound, which is usable in producing an oxidized compound by an oxidation reaction of a compound having a carbon-carbon double bond and at least one other functional group wherein the carbon-carbon double bond of the compound is oxidized by using a peroxide as an oxidizing agent. The catalyst has an MWW structure and is represented by the following composition formula (2):

$$xTiO_2 \cdot yM_2O_3 \cdot (1-x-2y)SiO_2 \quad \text{Composition formula (2)}$$

(wherein M represents at least one element selected from the group consisting of aluminum, boron, chromium, gallium and iron, x is a number of 0.0001 to 0.2 and y is a number of 0.0001 to 0.1).

In the above composition formula (2), the number "x" has the same meaning as in the composition formula (1) and the number "y" is also a molar ratio of constituent unit $M_2O_3$ present in the catalyst. Similarly to the composition formula (1), the ratio of x/(1−x−2y) represents merely a molar ratio of "titanium"/"silicon" and the ratio of y/(1−x−2y) represents merely a ratio of "at least one element in total selected from the group consisting of aluminum, boron, chromium, gallium and iron"/"silicon". Accordingly, these ratios do not exclude the presence of other elements in the catalyst according to the present invention in the second aspect. In the composition formula (2), y is a number of 0.0001 to 0.1, preferably 0.0001 to 0.05, more preferably 0.0001 to 0.03.

In the composition formula (2) according to the present invention in the second aspect, the number y can be determined from the component analysis values in a similar manner as in the case of the number x in the composition formula (1) according to the present invention in the first aspect. The form or state of the presence of $M_2O_3$ may be either within the framework or outside the framework. M is at least one element selected from the group consisting of aluminum, chromium, gallium and iron, and has a valence number of 3.

As used in the synthesis of MCM-22, an alkali metal such as sodium and potassium can be generally expected to function as a mineralizing agent, and therefore, the alkali metal may be used in the production of the catalyst according to the present invention in the first or second aspect for the purpose of accelerating the crystallization. However, in general, the alkali metal has a possibility of inhibiting the catalytic function of the crystalline titanosilicate, and therefore, it is preferred to remove the alkali metal from the crystalline titanosilicate by ion exchange or the like.

The MWW structure, which is one known structure of molecular sieves, is characterized in that it has a pore comprising a ring structure containing 10 oxygen atoms and has a super cage (0.7×0.7×1.8 nm). This structure has been approved by IZA after the publication of the above-mentioned Atlas. The details of the structure can be inspected, for example, on the homepage (http://www.iza-structure.org/) of the IZA Structure Commission (as of September, 2000). Examples of known molecular sieves having this structure may include MCM-22 (*Science, Vol.* 264, 1910 (1994)), SSZ-25 (European Patent No. No. 231860), ITQ-1 (*Chem. Mater.*, Vol. 8, 2415 (1996) and *J. Phys. Chem. B*, Vol. 102, 44 (1998)), ERB-1 (European Patent No. No. 203032) and PSH-3 (U.S. Pat. No. 449409). The molecular sieve having structural code of MWW can be identified by the pattern of its characteristic X-ray diffraction (hereinafter, simply referred to as "XRD"). The XRD pattern may also be available as a simulation pattern of ITQ-1, for example, on the above-mentioned homepage. Representative examples of the diffraction line may include those shown in Table 1 below.

TABLE 1

Diffraction Line Given by MWW Structure

| d/Å ± 0.1 | Relative Strength (s: strong, m: moderate, w: weak) |
| --- | --- |
| 12.3 ± 0.6 | s |
| 11.0 ± 0.6 | s |
| 8.8 ± 0.5 | s |
| 6.2 ± 0.4 | m |
| 5.5 ± 0.3 | w |
| 3.9 ± 0.2 | m |
| 3.7 ± 0.2 | w |
| 3.4 ± 0.2 | s |

The present invention in the third aspect will be described below. The present invention in the third aspect is a process for producing a crystalline MWW-type titanosilicate catalyst for providing an oxidized compound, comprising the following first and second steps:

First step a step of heating a mixture comprising a template compound, a titanium-containing compound, a boron-containing compound, a silicon-containing compound and water, to thereby obtain a precursor;

Second step a step of calcining the precursor obtained in the first step, to thereby obtain a crystalline titanosilicate.

The crystalline MWW-type titanosilicate catalyst for providing an oxidized compound according to the present invention can also be synthesized by a conventionally known direct synthesis method or a post-synthesis method such as an atom-planting method (with respect to the details of the atom-planting method, Yoshio Ono & Tastuaki Yashima "Science and Engineering of zeolites" (Jul. 10, 2000), p 142, Kodansha; and Peng Wu, Takayuki Komatsu, Tatsuaki Yashima, Shin-ichi Nakata, and Hiroshi Shouji, "Modification of mordenite acidity by isomorphous substitution of trivalent cations in the framework sites using the atom-planting method" Microporous Materials 12 (1997) 25–37 may be referred to.). In the case of the atom-planting method, the catalyst may be synthesized, for example, by preparing a molecular sieve having a MWW structure containing boron or aluminum, removing at least a part of boron or aluminum through a water vapor treatment or the like, and then contacting the resultant residue with a titanium compound such as titanium trichloride.

A more efficient production process for the MWW-type titanosilicate catalyst may include a production process according to the present invention in the third aspect. That is, the process for producing a crystalline MWW-type titanosilicate catalyst for providing an oxidized compound according to the present invention in the third aspect is a production process for a crystalline MWW-type titanosilicate catalyst for providing an oxidized compound, characterized in that the production process comprises two steps, i.e., a step of heating a mixture comprising a template compound, a titanium-containing compound, a boron-containing compound, a silicon-containing compound and water, to thereby obtain a precursor; and a step of calcining the resultant precursor, to thereby obtain a crystalline MWW-type titanosilicate for producing an oxidized compound.

At first, the above first step is described below. The first step in the process for producing the crystalline titanosilicate of the present invention in the third aspect is a step of heating a mixture comprising a template compound, a titanium-containing compound, a boron-containing compound, a silicon-containing compound and water, to thereby obtain a precursor.

The "template compound" as used herein is a compound having a function of, in the synthesis of zeolite having an MWW structure, determining the structure thereof and, particularly, of determining the shape of the pore. The template compound is not particularly limited, as long as it can be removed later by calcining. Examples thereof may generally include nitrogen-containing compounds. Specific examples of such a nitrogen-containing compound may include piperidine, hexamethyleneimine and/or a mixture thereof, but the template compound usable in the present invention is not limited to these specific compounds.

The titanium-containing compound which is usable in the first step is not particularly limited, as long as the titanium-containing compound can provide a gel-type product. Specific examples of the titanium-containing compound may include titanium oxide, titanium halide and tetraalkyl orthotitanates, but the titanium-containing compound usable in the present invention is not limited to these specific compounds. Among these, in view of easiness in the handling thereof, titanium halide and tetraalkyl orthotitanates are preferred. More specifically, titanium tetrafluoride, tetraethyl orthotitanate, tetrapropyl orthotitanate and tetrabutyl orthotitanate may suitably be used.

The boron-containing compound which is usable in the first step is not particularly limited. Preferred specific examples thereof may include boric acid, which can also be used in the form of a borate such as sodium borate.

The silicon-containing compound which is usable in the first step is not particularly limited. Specific examples thereof may include silicic acid, silicic acid salt, silicon oxide, silicon halide, fumed silicas, tetraalkyl orthosilicates and colloidal silica. In any of these cases, a silicon-containing compound having a high purity is preferred. More specifically, the silicon-containing compound may preferably have an alkali metal content such that the total moles of the alkali metal components is smaller than the moles of titanium, preferably 1/10 times or less the moles of titanium, more preferably 1/100 times or less the moles of titanium. Among these, in the case of colloidal silica, one having a smaller alkali content is preferred.

The ratio between titanium and silicon in the mixture to be used in the first step may preferably be 0.001 to 0.3:1 (titanium:silicon), more preferably 0.005 to 0.2:1 (titanium:silicon), particularly preferably 0.01 to 0.2:1 (titanium:silicon), in terms of the molar ratio therebetween.

The ratio between boron and silicon in the mixture to be used in the first step may preferably be 0.3 to 10:1 (boron:silicon), more preferably 0.5 to 5:1 (boron:silicon), particularly preferably 1 to 2:1 (boron:silicon), in terms of the molar ratio therebetween.

The ratio between water and silicon in the mixture to be used in the first step may preferably be 5 to 200:1 (water:silicon), more preferably 15 to 50:1 (water:silicon), in terms of the molar ratio therebetween.

The ratio between the template compound and silicon in the mixture to be used in the first step may preferably be 0.1 to 5:1 (template compound:silicon), more preferably 0.3 to 3:1 (template compound:silicon), particularly preferably 0.5 to 2:1 (template compound:silicon), in terms of the molar ratio therebetween.

These ratios of the mixture to be used in the first step are not particularly limited. However, in view of efficient provision of a high-activity crystalline MWW-type titanosilicate catalyst for providing an oxidized compound, each of the above-mentioned ranges is preferred. An element other than the elements described above can also be present together in the mixture to be used in the first step. However, if an alkali metal or an alkaline earth metal is present in a somewhat large amount, titanium may be prevented from entering into the framework. Therefore, the amount of an alkali metal or an alkaline earth metal may preferably be smaller. More specifically, for example, the total moles of an alkali metal and an alkaline earth metal may preferably be smaller than the moles of titanium. The total moles of an alkali metal and an alkaline earth metal may preferably be 1/10 times or less the moles of titanium, more preferably 1/100 times or less the moles of titanium.

The heating temperature to be used in the first step is not particularly limited. However, in the case of synthesizing a precursor, the heating may preferably be performed under hydrothermal reaction conditions. The term "hydrothermal reaction" as used herein means, as described in *Hyojun Kagaku Yogo Jiten* (*Standard Chemical Glossary*), Item "Hydrothermal Reaction", edited by the Chemical Society of Japan, published by Maruzen (Mar. 30, 1991), a synthesis or a modification reaction of a substance to be performed in the presence of water at high temperature, particularly to be performed in the presence of water at high temperature and high pressure. A synthesis reaction utilizing the hydrothermal reaction is called "hydrothermal synthesis". Therefore, in the first step, the heating may preferably be performed under hydrothermal synthesis conditions such that a mixture comprising a template compound, a titanium-containing compound, a boron-containing compound, a silicon-containing compound and water is charged into a closed container such as autoclave and is pressurized under heating. The heating temperature may preferably be in the range of from 110 to 200° C., more preferably from 120 to 190° C.

If the temperature in the hydrothermal synthesis is below this range, the intended product may not be obtained, or even if obtained, the heating may take a long period of time, and such a procedure is not suitable for a practical purpose. On the other hand, if the temperature exceeds this range, the yield of the intended product is disadvantageously decreased in the oxidation reaction using the resultant catalyst which is finally been obtained in this manner.

The hydrothermal synthesis may usually be performed for 2 hours to 30 days, preferably for 3 hours to 10 days. If the hydrothermal synthesis time is less than this range, the crystallization can be insufficient so that a high-performance catalyst may not be obtained. On the other hand, even if the hydrothermal synthesis is performed for a time period exceeding this range, the resultant catalytic activity is not substantially enhanced. In this case, an adverse effect such as conversion of the materials into another phase or an increase in the particle size can be caused disadvantageously.

Next, the second step is described below. The second step is a step of calcining the precursor obtained in the first step, to thereby obtain a crystalline MWW-type titanosilicate catalyst for providing an oxidized compound.

The method of calcining the precursor is not particularly limited and may be performed under known conditions in the usual calcination of a catalyst. The calcination may be performed in the closed system or in the flow system, and if desired, the calcination may be performed in an inert gas stream, such as nitrogen gas stream. The calcination temperature may preferably be in the range of from 200 to 700° C., more preferably from 300 to 650° C., particularly preferably from 400 to 600° C. If the calcination temperature is less than 200° C., the template compound may not be satisfactorily removed. On the other hand, if the calcination temperature exceeds 700° C., the MWW-type crystal structure may be destroyed, and as a result, this destruction may adversely affect the resultant catalytic performance.

The process for producing a crystalline MWW-type titanosilicate catalyst for providing an oxidized compound according to the present invention in the third aspect is described in detail below. The process for producing a catalyst according to the present invention in the third aspect is a process of converting a titanosilicate in an amorphous state into a precursor having a lamella phase called MCM-22(P) by using piperidine or hexamethyleneimine as a template, and using boron (boric acid) as a structure supporting agent (first step); and then calcining the precursor (second step), to thereby obtain a crystalline MWW-type titanosilicate catalyst for providing an oxidized compound.

There is described a more specific embodiment of the process for producing a crystalline MWW-type titanosilicate catalyst for providing an oxidized compound. For example, an aqueous solution of piperidine or hexamethyleneimine (template) is divided into two portions, tetraalkyl orthotitanate is added to one of the two portions and dissolved therein, a boron compound is added to the other of the two portions and dissolved therein, and silica is further added to each of the two portions, and then the resultant mixture are stirred, to prepare two kinds of homogenous gels containing titanium or boron.

These two kinds of gels are mixed with each other and thoroughly stirred, and thereafter the mixture is transferred to a closed container such as autoclave and subjected to a hydrothermal synthesis. The thus obtained solid product is separated from the mother liquor by filtration or the like, thoroughly washed with water and then dried. By calcining the thus obtained precursor, a crystalline MWW-type titanosilicate catalyst for providing an oxidized compound can be obtained.

The catalyst which is obtainable by the production process according to the present invention in the third aspect may be used as a catalyst for an oxidation reaction as it is. The boron which has been introduced inside or outside the framework present in the titanosilicate obtained by this production process, or the anatase phase which has resulted from the condensation of titanium itself which does not participate in an oxidation reaction may be removed at least partially by contacting the catalyst with an acid. By the contact of the catalyst with the acid, the thus obtained crystalline MWW-type titanosilicate catalyst for providing an oxidized compound can have a higher performance.

A certain effect may be obtained, when the catalyst is contacted with an acid before or after the calcination, or both before and after the calcination in the process for producing a crystalline MWW-type titanosilicate catalyst for providing an oxidized compound. However, a particularly enhanced effect can be obtained, when the catalyst in the precursor state is contacted with an acid before the calcination. In the latter case, the by-product anatase phase due to the calcination can be strongly suppressed.

The "contact with an acid" as used herein specifically means an operation such that a solution containing an acid or an acid itself is contacted with the precursor which has been obtained after the first step, or with the titanosilicate which has been obtained after the second step. The contacting method is not particularly limited. The contacting method may be a method of spraying or applying an acid or an acid solution to the precursor or titanosilicate, or a method of dipping the precursor or titanosilicate in an acid or an acid solution. The method of dipping the precursor or titanosilicate in an acid or an acid solution is simple and easy, and therefore this method is preferred.

The acid to be used for the above-mentioned acid contact may be an inorganic acid, an organic acid or a salt of these acids. Specific examples of preferred inorganic acids may include hydrochloric acid, sulfuric acid, nitric acid and phosphoric acid. Specific examples of preferred organic acids may include formic acid, acetic acid, propionic acid and tartaric acid. Examples of the salt of these acids may include sodium salt, potassium salt, calcium salt, magnesium salt and ammonium salt of these acids.

The contact with an acid may be performed either before or after the calcination as described above, but may preferably be performed before the calcination so as to attain an enhanced effect. A solid substance such as precursor is dipped in an acid solution in an amount of approximately from 5 to 100 ml per one gram of the solid substance, and kept therein for a predetermined time. Thereafter, the solid is recovered from the acid solution by filtration or the like, and then thoroughly washed with a solvent. Stirring is not always necessary but may be performed.

In the case of using the acid in the form of a solution, the solvent is not particularly limited. Specific examples thereof may include water, alcohols, ethers, esters and ketones. Among these, water is preferred.

The acid concentration is not particularly limited but may suitably be on the order of 0.1 to 10 mol/l. The temperature may be in the range of from 0 to 200° C., but may preferably be from 50 to 180° C., more preferably from 60 to 150° C. The treatment time may be from 0.1 hour to 3 day, but may suitably be from 2 hours to 1 day.

The present invention in a fourth aspect is described below. The present invention in the fourth aspect is a process for producing an oxidized compound comprising: performing an oxidation reaction of a compound having a carbon-carbon double bond and at least one of other functional group wherein the carbon-carbon double bond of the compound is oxidized by using a peroxide as an oxidizing agent in the presence of the crystalline MWW-type titanosilicate catalyst for providing an oxidized compound according to the present invention in the first or second aspect. According to the production process for an oxidized compound according to the present invention in the fourth aspect, the oxidation reaction of a carbon-carbon double bond only can be selectively performed substantially without affecting other functional groups of the compound having a carbon-carbon double bond and at least one of other functional group. Needless to say, other functional groups may be simultaneously reacted, to thereby obtain an entirely different product. Such a case, of course, may be included in the scope of the present invention in the fourth aspect.

Specific examples of the peroxide which is usable in the present invention in the fourth aspect may include hydrogen peroxide and organic peroxides. Examples of the organic peroxide may include tert-butyl hydroperoxide, tert-amyl hydroperoxide, cumene hydroperoxide, ethylbenzene hydroperoxide, cyclohexyl hydroperoxide, methylcyclohexyl hydroperoxide, tetralin (i.e., tetrahydronaphtalene) hydroperoxide, isobutylbenzene hydroperoxide, ethylnaphthalene hydroperoxide and peracetic acid. However, the peroxides usable in the present invention are not limited to these specific compounds. These peroxides may also be used in combination of two or more species thereof.

The peroxide to be used for such a purpose may particularly preferably be hydrogen peroxide. An aqueous hydrogen peroxide solution having any of various concentrations may be used. Examples of such concentrations may include, e.g., 30 mass %, 60 mass %, 90 mass % or the like. The amount of peroxide to be added to the reactant is not particularly limited, and the amount may be equivalent or more to the carbon-carbon double bond of the compound having a carbon-carbon double bond and at least one of other functional group, which is a raw material to be subjected to an oxidation reaction, or the amount may be equivalent or less, depending on the conditions.

The compound having a carbon-carbon double bond and at least one of other functional group for use in the process for producing an oxidized compound according to the present invention in the fourth aspect is not particularly limited, and may be any compound as long as it has a carbon-carbon double bond and at least one other functional group within one molecule thereof. In this case, a compound containing two or more carbon-carbon double bonds, of course, may be included within the definition of the above "compound having a carbon-carbon double bond and at least one of other functional group".

Specific examples of the other functional group may include an alkenyl group, an alkynyl group, an aryl group, an arene group, an alcohol group, a phenol group, an ether group, an epoxide group, a halogen group, an aldehyde group, a ketone group, a carbonyl group, an ester group, an amide group, a cyanate group, an isocyanate group, a thiocyanate group, an amine group, a diazo group, a nitro group, a nitrile group, a nitroso group, a sulfide group, a sulfoxide group, a sulfone group, a thiol group, an orthoester group, a urea group and imine group. However, the "other functional group" usable in the present invention is not limited to these specific compounds. Two or more of the same functional group may be contained in one molecule, and/or two or more kinds of functional groups may be contained in one molecule.

More specific examples of the compound having a carbon-carbon double bond and at least one other functional group may include allyl ethers, compounds having from 3 to 10 carbon atoms, ethers of polyhydric alcohol, and carboxylic acid esters. Of course, these compounds may also be used in combination of two or more species thereof.

More specifically, examples of the allyl ethers may include allyl methyl ether, allyl ethyl ether, allyl propyl ether, allyl butyl ether, allyl vinyl ether and diallyl ether.

Examples of the compounds having from 3 to 10 carbon atoms may include allyl alcohol, allyl bromide, allyl chloride, acrolein, methacrolein and acrylic acid.

Examples of the ethers of polyhydric alcohol may include ethylene glycol monoalkenyl ether, ethylene glycol dialkenyl ether, 1,2-propanediol monoalkenyl ether, 1,2-propanediol dialkenyl ether, 1,3-propanediol monoalkenyl ether, 1,3-propanediol dialkenyl ether, 1,2-butanediol monoalkenyl ether, 1,2-butanediol dialkenyl ether, 1,3-butanediol monoalkenyl ether, 1,3-butanediol dialkenyl ether, 1,4-butanediol monoalkenyl ether, 1,4-butanediol dialkenyl ether, and pentaerythritol monoalkenyl ether, pentaerythritol dialkenyl ether, pentaerythritol trialkenyl ether and pentaerythritol tetraalkenyl ether, trimethylolpropane monoalkenyl ether, trimethylolpropane dialkenyl ether, and trimethylolpropane trialkenyl ether.

Examples of the carboxyllic acid esters may include allyl formate, allyl acetate, allyl tartrate, allyl propionate and allyl methacrylate.

Examples of particularly preferred combination may include a combination such that the compound having a carbon-carbon double bond and at least one of other functional group is diallyl ether, allyl acetate, allyl methacrylate or allyl alcohol and the oxidizing agent is hydrogen peroxide.

The amount of the crystalline MWW-type titanosilicate catalyst for providing an oxidized compound used in the process for producing an oxidized compound according to the present invention in the fourth aspect is not particularly limited. The preferred range thereof may vary depending on the kind of oxidation reaction, the reaction temperature, the reactivity and temperature of the substrate or reactant, the concentration of peroxide, the kind and concentration of solvent, and the reaction form or type (e.g., batch system, continuous system). In a case where the catalyst is used in a slurry system, the amount of the catalyst may usually be in the range of from 0.1 to 20 mass %, more preferably from 0.5 to 10 mass %, in terms of the concentration of the catalyst in the reactant mixture. In the case of a fixed-bed flow reaction system, the apparent amount of the catalyst may preferably be larger than the above-mentioned range.

The shape or form of the crystalline MWW-type titanosilicate catalyst for providing an oxidized compound is not particularly limited. The form may be a powder, microspheres, pellets or extrusion-molded articles, or the catalyst may also be in a form such that it is supported on a support or carrier. In the molding of the catalyst, a binder may be used. The binder or support for such a purpose may preferably be a substance which is substantially non-acidic or weakly acidic, and which does not accelerate the decomposition reaction of the peroxide or the decomposition reaction of the intended oxidized compound.

The oxidation reaction in the process for producing an oxidized compound according to the present invention in the fourth aspect may be performed without using a solvent or in the presence of an appropriate solvent. Examples of the appropriate solvent may include alcohols, ketones, nitrites and water. Specific examples of alcohols may include methanol, ethanol, 1-propanol, 2-propanol, 1-butanol, 2-butanol, tert-butanol, amyl alcohol, ethylene glycol, propylene glycol and 1,2-butanediol. Specific examples of ketones may include acetone, methyl ethyl ketone and diethyl ketone. Specific examples of nitrites may include acetonitrile, propionitrile and benzonitrile. These may be used singly or as a mixture thereof. Among these solvents, preferred are acetone, acetonitrile and water, and more preferred is acetonitrile.

In the process for producing an oxidized compound according to the present invention in the fourth aspect, the reaction temperature at the oxidation reaction, which is not particularly limited, may preferably be from 0 to 150° C., more preferably from 10 to 100° C. If the reaction temperature is less than 0° C., the reaction rate is low and this temperature is not suitable for practical purposes. On the other hand, if the temperature exceeds 150° C., a decomposition reaction of the peroxide may seriously proceed and, further, a decomposition reaction of the intended product may disadvantageously be accelerated.

The oxidation reaction is generally an exothermic reaction, and therefore, the heat of reaction may preferably be removed by a suitable method so as to control the reaction temperature to a constant range. The reaction pressure is not particularly limited.

The oxidation reaction in the process for producing an oxidized compound according to the present invention in the fourth aspect may be performed by any method in a batch system, a continuous system or a semi-continuous system, e.g., by using a suitable reactor or reaction apparatus such as fixed bed reactor, fludized-bed reactor, moving-bed reactor, tank reactor, stirring slurry-type reactor, continuous stirred tank reactor (CSTR). With respect to the mixture containing a crystalline MWW-type titanosilicate catalyst for providing an oxidized compound, a compound having a carbon-carbon double bond and at least one other functional group and a peroxide, these components constituting the mixture may be mixed partially or all at once or may be mixed in sequence or in order. It is also possible to mix the two species selected from the three species of these components (i.e., the catalyst, the compound having a carbon-carbon double bond and at least one of other functional group, and the peroxide), and then mix the remaining one species of these components into such a mixture.

In this reaction, the intended oxidized compound (reaction product) may be separated by a separation/purification method used in an ordinary purification procedure. More specifically, for example, when the reaction is performed in a batch system, when the amount of the oxidized compound which has been produced reaches a value in the desired region, the oxidized compound may be separated and recovered from the reaction mixture by using any known method such as fractional distillation, extract distillation or liquid-liquid extraction.

In the case of a slurry-type reactor, the crystalline MWW-type titanosilicate catalyst for providing an oxidized compound can be recovered by a suitable method such as filtration or centrifugation, and the thus recovered catalyst can be reused as a catalyst for oxidation reaction.

In the case of a fixed bed-type reactor, the crystalline MWW-type titanosilicate catalyst for providing an oxidized compound can be easily separated from the product (oxidized compound), the solvent, the unreacted compound having a carbon-carbon double bond and at least one of other functional group and the peroxide, while the catalyst remains being held in the reactor.

In the process for producing an oxidized compound according to the present invention in the fourth aspect, at least one of the recovered crystalline MWW-type titanosilicate catalyst for providing an oxidized compound, the unreacted compound having a carbon-carbon double bond and at least one of other functional group and the peroxide can be reused, after purification by an appropriate method or without purification thereof.

In the present invention in the fourth aspect, the recovered crystalline MWW-type titanosilicate catalyst for providing an oxidized compound generally has a tendency such that the activity thereof is decreased each time it is used repeatedly, and the catalyst after the repeated use cannot exhibit its initial activity. In such a case, the recovered catalyst may be regenerated or reproduced. The recovered catalyst may be regenerated by a conventionally known method. More specifically, the catalyst may be regenerated so that it has an initial activity, for example, by calcining the catalyst in air at a temperature of 100 to 600° C.

EXAMPLES

Hereinbelow, the present invention will be described in further detail by referring to the Examples. However, these Examples are set forth only to show the outline of the present invention and the present invention should not be construed as being limited to these specific Examples.

Description of Terms in Examples and Comparative Examples

Method of Calculating Conversion of Allyl Alcohol

The molar ratio of allyl alcohol which has been consumed in the reaction, based on the allyl alcohol which has been charged prior to the reaction. The allyl alcohol consumed in the reaction was calculated from the increase and decrease of allyl alcohol between the amounts thereof before and after the reaction.

Method of Calculating Selectivity for Glycidol

The molar ratio between glycidol and glycerin which has been calculated from the results of analysis of a filtrate after the reaction.

Method of Calculating Conversion of Hydrogen Peroxide

The ratio of hydrogen peroxide which has been consumed in the reaction based on the hydrogen peroxide which has been charged prior to the reaction. The hydrogen peroxide consumed in the reaction was calculated from the increase and decrease of hydrogen peroxide between the amounts thereof before and after reaction.

Calculation of Effective Ratio of Hydrogen Peroxide

The effective ratio of hydrogen peroxide indicates a ratio of hydrogen peroxide which has been obtained by subtracting the amount of the hydrogen peroxide consumed in the decomposition into oxygen, from the amount of the hydrogen peroxide consumed in the reaction. That is, the effective ratio of hydrogen peroxide is the ratio of hydrogen peroxide consumed in the epoxidation reaction, based on the total amount of the consumed hydrogen peroxide.

Yield of Epoxide

The yield of the epoxide compound (intended oxidized product) based on hydrogen peroxide after the completion of the oxidation reaction using the hydrogen peroxide. This yield indicates a molar ratio of the amount of epoxide compound produced to the amount of the hydrogen peroxide charged into the reaction.

Reduction Ratio of Catalytic Activity

This ratio indicates a decrement in the molar amount of the epoxide compound which has been produced by using a repeatedly used catalyst, based on the molar amount of the epoxide compound which has been produced by using an unused catalyst.

Apparatuses for Analysis in Examples and Comparative Examples

Method of Elemental Analysis for Titanosilicate

A sample of titanosilicate was accurately weighed in a Teflon (polytetrafluoroethylene) beaker, and 1 ml of hydrofluoric acid (concentration: 50% by mass) was added to the beaker so as to dissolve the titanosilicate therein. Then, pure water was added to the beaker until the concentrations of the respective elements to be measured were in the range of 0–10 ppm. The thus obtained solution was subjected to a component analysis for titanium, silicon and boron by using a desktop-type plasma emission analysis apparatus (SPS 1700, mfd. by Seiko Denshi Kogyo K.K.). In this analysis, the titanium concentration was measured by using a wavelength of 334.9410 nm, the silicon concentration was measured by using a wavelength of 251.611 nm, and the boron concentration was measured by using a wavelength of 249.7730 nm.

Analysis of Organic Compound Concentration in Filtrate of Reaction Mixture

The organic compound concentration was measured by using the following gas chromatography analyzing apparatus under the following analyzing conditions.

In this analysis, an internal standard method was used. More specifically, 1 ml of 1,4-dioxane as an internal standard was added to 10 ml of a reaction solution to prepare a solution to be analyzed and 0.4 Al of the resultant analysis solution was injected into the gas chromatograph.

Gas chromatograph:
 GC-14B mfd. by Shimadzu Seisakusho
Column:
 capillary column TC-WAX (length: 30 m, internal diameter: 0.25 mm, column wall thickness: 0.25 $\mu$m)
Carrier gas:
 nitrogen (split ratio: 20, column flow rate: 2 ml/min)
Temperature condition:
 The temperatures of the detector and the vaporization chamber were 200° C. The column temperature was kept at 50° C. for 5 minutes from the initiation of analysis, then was elevated to 150° C. at a temperature-rising rate of 10° C./min, kept at 150° C. for 10 minutes, thereafter elevated to 200° C. at a temperature-rising rate of 10° C./min and kept at this temperature for 25 minutes.
Detector:
 FID ($H_2$ pressure: 70 kPa, air pressure: 100 kPa).

Analysis of Hydrogen Peroxide Concentration in Filtrate of Reaction Mixture

A potentiometric titration was performed by using an automatic potentiometric titrating apparatus AT-012 (mfd. by Kyoto Denshi Kagaku Kogyosha) and by using an aqueous solution containing Ce(IV) as a titration reagent, to thereby measure the hydrogen peroxide concentration in the filtrate of a reaction mixture. More specifically, 40 ml of ion-exchanged water was added to a 100 ml-glass beaker, and then about 0.3 g of a sample of the filtrate of the reaction mixture to be measured was accurately weighed out in the beaker. Thereafter, potentiometric titration was performed by means of the above automatic potentiometric titrating apparatus by slowly adding to the beaker a 0.1 mol/l-aqueous solution which had been prepared by using tetraammonium cerium sulfate dihydrate (produced by Wako Pure Chemical Industries, Ltd.). The hydrogen peroxide concentration was calculated from the amount of the above 0.1 mol/l-aqueous tetraammonium cerium sulfate solution which had been required for the potentiometric titration until the end point thereof, and the weight of the filtrate of the reaction mixture which had been used for the analysis.

Example 1

Production of Catalyst 1

182.5 g of piperidine (purity: 98%, produced by Wako Pure Chemical Industries, Ltd.) (hereinafter, piperidine is simply referred to as "PI" in some cases) was dissolved in 513 g of ion-exchanged water at 25° C. to prepare an aqueous piperidine solution. This aqueous piperidine solution was divided into two equal portions. Under vigorous stirring, 18.0 g of tetrabutyl orthotitanate (purity: 95%, produced by Wako Pure Chemical Industries, Ltd.) was added to one of the two portions, and 124.2 g of boric acid (purity: 99.5%, produced by Wako Pure Chemical Industries, Ltd.) was added to the other of the two portions. The hydrolysis reaction of tetrabutyl orthotitanate was caused to completely proceed under stirring for 30 minutes, and thereafter, 45 g of fumed silica (trade name: Cab-o-sil M7D, mfd. by Cabot Co.) was added to each of the two resultant solutions containing titanium or boron. After the addition of silica, the solutions were stirred for 1 hour, to thereby obtain two kinds of homogenous gel-like products. These two kinds of gels were mixed with each other and the resultant mixed gel was continuously stirred for 1 hour and 30 minutes, to thereby obtain a mixture having a molar ratio of $1.SiO_2:0.033\text{-}TiO_2:0.67.B_2O_3:1.4.PI:19.H_2O$.

This gel was transferred to 2-liter autoclave equipped with a Teflon-made inner cylinder disposed in the autoclave, stirred therein at a temperature of 130° C. and a revolution number of 100 rpm for 24 hours, subsequently stirred at a temperature of 150° C. and at 100 rpm for 24 hours, and further stirred at a temperature of 170° C. and at 100 rpm for 120 hours. After the completion of the stirring, the content in the autoclave was cooled to 25° C., a solid product was separated from the content by filtration, and the resultant solid product was washed by using ion-exchanged water. The washing was repeated until the pH of washing water became 9 or less. The thus obtained solid product was dried at a temperature of 50° C. To 1 g of the resultant solid product, 20 ml of 6 mol/l-nitric acid was added to perform an acid treatment at a temperature of 100° C. for 20 hours. After the completion of the acid treatment, the solid was collected by filtration and calcined in an atmosphere of air at a temperature of 530° C. for 10 hours, to thereby obtain final intended product of MWW-type titanosilicate Catalyst 1.

The molar ratio of titanium/silicon and the molar ratio of boron/silicon of Catalyst 1 were measured in the above-mentioned manner. The results are shown in Table 2 appearing hereinbelow.

Example 2

Production of Catalyst 2

MWW-type titanosilicate Catalyst 2 was obtained in the same manner as in Example 1 except for using 1.0 mol/l-sulfuric acid in place of 6 mol/l-nitric acid in the acid treatment.

The molar ratio of titanium/silicon and the molar ratio of boron/silicon of Catalyst 2 were measured. The results are shown in Table 2 appearing hereinbelow.

Example 3

Production of Catalyst 3

MWW-type titanosilicate Catalyst 3 was obtained in the same manner as in Example 1 except for using 2.0 mol/l-sulfuric acid in place of 6 mol/l-nitric acid in the acid treatment.

The molar ratio of titanium/silicon and the molar ratio of boron/silicon in Catalyst 3 were measured. The results obtained are shown in Table 2 appearing hereinbelow.

Example 4

Production of Catalyst 4

182.5 g of PI (purity: 98%, produced by Wako Pure Chemical Industries, Ltd.) was dissolved in 513 g of ion-exchanged water at 25° C. to prepare an aqueous piperidine solution. This aqueous piperidine water was divided into two equal portions. Under vigorous stirring, 18.0 g of tetrabutyl orthotitanate (purity: 95%, produced by Wako Pure Chemical Industries, Ltd.) was added to one of the two portions and 124.2 g of boric acid (purity: 99.5%, produced by Wako Pure Chemical Industries, Ltd.) was added to the other of the two portions. The hydrolysis reaction of tetrabutyl orthotitanate was caused to completely proceed under stirring for 30 minutes, and thereafter 45 g of fumed silica (Cab-o-sil M7D) was added to each of the two solutions containing titanium or boron. After the addition of silica, the solutions were stirred for 1 hour, to thereby obtain two kinds of homogenous gel-like products. These two gels were mixed with each other and the resultant mixed gel was continuously stirred for 1 hour and 30 minutes, to thereby obtain a mixture having a molar ratio of $1.SiO_2:0.033.TiO_2:0.67.B_2O_3:1.4.PI:19.H_2O$.

This gel was transferred to a 2-liter autoclave equipped with a Teflon inner cylinder disposed therein, stirred at a temperature of 130° C. and at 100 rpm for 24 hours, subsequently stirred at a temperature of 150° C. and a revolution number of 100 rpm for 24 hours, and further stirred at a temperature of 170° C. and at 100 rpm for 120 hours. After the completion of the stirring, the content in the autoclave was cooled to 25° C., a solid product was separated from the content by filtration, and the solid product was washed by using ion-exchanged water. The washing was repeated until the pH of washing water became 9 or less. The thus obtained solid product was calcined at a temperature of 530° C. for 10 hours, to thereby obtain final intended product of MWW-type titanosilicate Catalyst 4.

The molar ratio of titanium/silicon and the molar ratio of boron/silicon of Catalyst 4 were measured. The results are shown in Table 2 appearing hereinbelow.

Example 5: Production of Catalyst 5

182.5 g of PI (purity: 98%, produced by Wako Pure Chemical Industries, Ltd.) was dissolved in 513 g of ion-exchanged water at 25° C. to prepare an aqueous piperidine solution. This aqueous piperidine water was divided into two equal portions. under vigorous stirring, 18.0 g of tetrabutyl orthotitanate (purity: 95%, produced by Wako Pure Chemical Industries, Ltd.) was added to one of the two portions and 124.2 g of boric acid (purity: 99.5%, produced by Wako Pure Chemical Industries, Ltd.) was added to the other of the two portions. The hydrolysis reaction of tetrabutyl orthotitanate was caused to completely proceed under stirring for 30 minutes, 45 g of fumed silica (Cab-o-sil M7D) was added to each of the two solutions containing titanium or boron. After the addition of silica, the solutions were stirred for 1 hour, to thereby obtain two kinds of homogenous gel-like products. These two gels were mixed with each other and the resultant mixed gel was continuously stirred for 1 hour and 30 minutes, to thereby obtain a mixture having a molar ratio of $1SiO_2:0.033.TiO_2:0.67.B_2O_3:1.4.PI:19.H_2O$.

This gel was transferred to 2-liter autoclave equipped with a Teflon inner cylinder disposed therein, stirred at a temperature of 130° C. and at 100 rpm for 24 hours, then stirred at a temperature of 150° C. and at 100 rpm for 24 hours, further stirred at a temperature of 170° C. and at 100 rpm for 120 hours. After the completion of the stirring, the content in the autoclave was cooled to 25° C., a solid product was separated from the content by filtration, and the solid product was washed by using ion-exchanged water. The washing was repeated until the pH of the washing water became 9 or less. The thus obtained solid product was dried at a temperature of 50° C. To 1 g of the resultant solid product, 20 ml of 6 mol/l-nitric acid was added to perform an acid treatment at a temperature of 100° C. for 20 hours. After the completion of the acid treatment, the solid was collected by filtration. To 1g of the resultant solid product, 20 ml of 2 mol/l-nitric acid was further added to perform an acid treatment at a temperature of 100° C. for 20 hours. The thus treated solid was calcined at a temperature of 530° C. for 10 hours, to thereby obtain final intended product of MWW-type titanosilicate Catalyst 5.

The molar ratio of titanium/silicon and the molar ratio of boron/silicon of Catalyst 5 were measured. The results are shown in Table 2 appearing hereinbelow.

The molar ratio of titanium/silicon and the molar ratio of boron/silicon of Catalysts 1 to 5 obtained in Examples 1 to 5 are shown in Table 2 appearing hereinbelow.

TABLE 2

| | No. | Molar Ratio of Titanium/Silicon | Molar Ratio of Boron/Silicon |
|---|---|---|---|
| Example 1 | Catalyst 1 | 0.0217 | 0.0204 |
| Example 2 | Catalyst 2 | 0.0132 | 0.0244 |
| Example 3 | Catalyst 3 | 0.0068 | 0.0294 |
| Example 4 | Catalyst 4 | 0.0323 | 0.0910 |
| Example 5 | Catalyst 5 | 0.0074 | 0.0016 |

Example 6

Production of Oxidized Compound using MWW-type Titanosilicate Catalyst 1

To a 20 ml-volume three-neck flask equipped with a thermometer, a reflux condenser and a magnetic stirrer, 0.58 g (10 mmol) of allyl alcohol and 3.9 g (5 ml) of acetonitrile were added, and MWW-type titanosilicate Catalyst 1 (70 mg) obtained in Example 1 was charged into the flask. The flask was heated in a water bath at 60° C. and the mixture was vigorously stirred. Immediately after the temperature of the reaction mixture reacted 57° C., 1.1 g (10 mmol as hydrogen peroxide) of an aqueous 30 mass %-hydrogen peroxide solution was added to the reaction system. This point was taken as the reaction initiation time, and the stirring was continued, until 30 minutes was counted from the reaction initiation. After 30 minutes from the reaction initiation, the reaction mixture was immediately cooled with ice to stop the reaction. Thereafter, the reaction mixture was filtered to separate unreacted allyl alcohol, unreacted hydrogen peroxide, water, product and solvent from the catalyst. At this time, the concentration of organic substances in the filtrate was analyzed by gas chromatography and the concentration of unreacted hydrogen peroxide was determined by potentiometric titration using Ce(IV). The results of the reaction are shown in Table 3 appearing hereinbelow. The conversion of allyl alcohol was 87.0% and the selectivity for glycidol as the product epoxide compound was 99.9%. Further, the conversion of hydrogen peroxide was 87.9% and the effective ratio of hydrogen peroxide was 99.0%.

TABLE 3

| | Kind of Catalyst | | | | Conversion (%) | | Selectivity (mol %)[*3] | | Effective Ratio of Hydrogen Peroxide (%) |
|---|---|---|---|---|---|---|---|---|---|
| | No. | Molar Ratio of Titanium/Silicon[*5] | Molar Ratio of Boron/Silicon[*5] | Solvent Used in Reaction | Allyl Alcohol[*1] | Hydrogen Peroxide[*2] | Glycidol | Glycerin | |
| Example 6 | Catalyst 1 | 0.0217 | 0.0204 | Acetonitrile | 87.0 | 87.9 | 99.9 | 0.1 | 99.0 |
| Example 7 | Catalyst 2 | 0.0132 | 0.0244 | Acetonitrile | 42.6 | 45.3 | 98.1 | 1.9 | 94.1 |
| Example 8 | Catalyst 3 | 0.0068 | 0.0294 | Acetonitrile | 16.2 | 17.2 | 92.1 | 7.9 | 94.2 |
| Example 9 | Catalyst 4 | 0.0323 | 0.0910 | Acetonitrile | 3.1 | 4.9 | 32.0 | 68.0 | 63.5 |
| Example 10 | Catalyst 5 | 0.0074 | 0.0016 | Acetonitrile | 12.4 | 13.4 | 94.5 | 5.5 | 92.3 |
| Example 11 | Catalyst 1 | 0.0217 | 0.0204 | Water | 82.3 | 97.6 | 99.9 | 0.1 | 84.3 |
| Example 12 | Catalyst 1 | 0.0217 | 0.0204 | Ethanol | 32.5 | 33.0 | 91.0 | 9.0 | 98.5 |
| Comparative Example 1 | MFI-type | 0.0222 | — | Acetonitrile | 26.4 | 28.9 | 87.9 | 12.1 | 91.3 |

[*1]Conversion of allyl alcohol: consumed allyl alcohol (mol)/raw material allyl alcohol (mol) × 100 (%)
[*2]conversion of hydrogen peroxide: consumed hydrogen peroxide (mol)/raw material hydrogen peroxide (mol) × 100 (%)
[*3]Selectivity for glycidol: glycidol (mol)/[glycidol (mol) + glycerin (mol)] × 100 (mol %)
Selectivity for glycerin: glycerin (mol)/[glycidol (mol) + glycerin (mol)] × 100 (mol %)
[*4]Effective ratio of hydrogen peroxide: [glycidol (mol) + glycerin (mol)]/consumed hydrogen peroxide (mol) × 100 (%)
[*5]Molar ratio (calculated by ICP emission spectroscopic analysis)

Example 7

Production of Oxidized Compound Using MWW-type Titanosilicate Catalyst 2

The same operation as in Example 6 was performed except for using the Catalyst 2 obtained in Example 2 instead of the Catalyst 1 obtained in Example 1. The results of the reaction are shown in Table 3 appearing hereinabove.

Example 8

Production of Oxidized Compound Using MWW-type Titanosilicate Catalyst 3

The same operation as in Example 6 was performed except for using the Catalyst 3 obtained in Example 3 instead of the Catalyst 1 obtained in Example 1. The results of the reaction are shown in Table 3 appearing hereinabove.

Example 9

Production of Oxidized Compound Using MWW-type Titanosilicate Catalyst 4

The same operation as in Example 6 was performed except for using the Catalyst 4 prepared in Example 4. The results of the reaction are shown in Table 3 appearing hereinabove.

Example 10

Production of Oxidized Compound Using MWW-type Titanosilicate Catalyst 5

The same operation as in Example 6 was performed except for using the Catalyst 5 prepared in Example 5. The results of the reaction are shown in Table 3 appearing hereinabove.

Example 11

Examination of Reaction Solvent

The same operation as in Example 6 was performed except for adding 5 g (5 ml) of water as a solvent in place of using acetonitrile as a solvent used in Example 6. The results of the reaction are shown in Table 3 appearing hereinabove.

Example 12

The same operation as in Example 6 was performed except for adding 3.9 g (5 ml) of ethanol as a solvent in place of using acetonitrile as a solvent used in Example 6. The results of the reaction are shown in Table 3 appearing hereinabove.

Comparative Example 1

Production of MFI-type Titanosilicate Catalyst and Production of Oxidized Compound

To 500 ml-volume beaker equipped with a magnetic stirrer, 62.5 g of tetraethyl orthosilicate (produced by Wako Pure Chemical Industries, Ltd.) was added and subsequently, 107 g of an aqueous 20 mass % tetrapropyl ammonium hydroxide solution (produced by Tokyo Kasei Kogyo Co., Ltd.) was added at a temperature of 30° C. over 10 minutes. The resultant mixture was stirred for 1.0 hour and, thereafter, a mixture containing 38 g of isopropyl alcohol (produced by Wako Pure Chemical Industries, Ltd.) and 14 g of tetra orthotitanate (produced by Tokyo Kasei Kogyo Co., Ltd.) was added over 30 minutes. The resultant mixture was stirred at 30° C. for 30 minutes, and thereafter the mixture was heated by using a water bath at 80° C. and was continuously stirred for 2 hours. To the thus obtained mixture, 230 g of water was added and the resulting solution was transferred to a autoclave equipped with a Teflon inner cylinder disposed therein and subjected to hydrothermal synthesis at 175° C. for 48 hours. After the completion of hydrothermal synthesis, the contents of the autoclave were taken out therefrom and centrifuged to separate the solid product. The thus obtained solid product was washed with distilled water in the content. After the completion of the washing, the product was calcined at 500° C. for 8 hours in the presence of air to remove organic substances. The product after the calcination was further washed for 12 hours by using 20 ml of an aqueous 1.0 mol/l nitric acid solution per 1 g of the solid and after the completion of acid washing, the solid product was separated by filtration. Subsequently, this solid product was calcined at 500° C. for 12 hours in the presence of air, to thereby obtain an intended MFI-type titanosilicate catalyst having a molar ratio of titanium/silicon of 0.0222.

The same operation as in Example 6 was performed except for using this MFI-type titanosilicate catalyst instead of the Catalyst 1 obtained in Example 1. The results of the reaction are shown in Table 3 appearing hereinabove.

Example 13

Repeated use

To a 20 ml-volume three-neck flask equipped with a thermometer, a reflux condenser and a magnetic stirrer, 0.23 g (4 mmol) of allyl alcohol and 7.9 g (10 ml) of acetonitrile were added, and MWW-type titanosilicate Catalyst 1 (100 mg) obtained in Example 1 was charged into the flask. The resulting mixture was heated in a water bath at 60° C. under vigorous stirring. Immediately after the temperature of the reaction mixture reached 57° C., 0.14 g (4 mmol as hydrogen peroxide) of 30 mass %-hydrogen peroxide was added to the reaction system. This point was taken as the reaction initiation time, and the stirring was continued until 0.5 hours was counted from the reaction initiation. After 0.5 hours from the reaction initiation, the reaction mixture was immediately cooled with ice to stop the reaction. Thereafter, the reaction mixture was filtered to separate unreacted allyl alcohol, unreacted hydrogen peroxide, water, product and solvent from the catalyst. At this time, the concentration of organic substances in the thus obtained filtrate was analyzed by gas chromatography and the concentration of unreacted hydrogen peroxide was determined by potentiometric titration using Ce(IV).

After the catalyst recovered by filtration was dried in a dryer at 80° C. for 6 hours in an atmosphere of air, a second-time reaction was performed under the same conditions as in the first-time reaction described above. After the completion of reaction, the mixture was filtered in the same manner as in the first-time reaction to separate the filtrate from the catalyst. Then, the filtrate was analyzed and the catalyst was recovered in the same manner as in the first-time reaction.

Again, the catalyst recovered after the second-time reaction was dried, a third-time reaction was performed under the same conditions as in the first and second-time reactions, and after the completion of reaction, the mixture was separated and analyzed in the same manner as in the first and second-time reactions. In such a manner, the reaction was performed three times in total. The results of the reaction are shown in the following Table 4. The reduction ratio of activity, indicating the deterioration of catalyst, was 2% in the second-time reaction and 10% in the third-time reaction.

TABLE 4

|  | Kind of Catalyst | Number of Use | Yield of Glycidol (%)*1 | Reduction Ratio of Activity (%)*3 |
|---|---|---|---|---|
| Example 13 | Catalyst 1 | 1st time | 88.3 | 0 |
|  |  | 2nd time | 86.7 | 2 |
|  |  | 3rd time | 79.5 | 10 |
| Comparative Example 2 | MFI-type*2 | 1st time | 28.4 | 0 |
|  |  | 2nd time | 20.5 | 28 |
|  |  | 3rd time | 19.8 | 31 |

*1 Yield of glycidol: amount of glycidol produced (mol)/amount of raw material hydrogen peroxide (mol) × 100 (%)
*2 MFI-type titanosilicate: molar ratio of titanium/silicon = 0.0222
*3 Reduction ratio of activity: [(yield of glycidol at first-time) − (yield of glycidol at second or third-time)/(yield of glycidol at first-time) × 100 (%)

Comparative Example 2

The same operation as in Example 11 was performed except for using the MFI-structure titanosilicate catalyst having a molar ratio of titanium/silicon of 0.0222 obtained in Comparative Example 1 instead of the Catalyst 1 obtained in Example 1. The results of the reaction are shown in Table 4 appearing hereinabove. The reduction ratio of activity, indicating the deterioration of catalyst, was 28% at the second-time reaction and 31% 20 at the third-time reaction.

Example 14

Examination of Reaction Substrate

To a 20 ml-volume three-neck flask equipped with a thermometer, a reflux condenser and a magnetic stirrer, 0.98 g (10 mmol) of diallyl ether and 3.9 g (5 ml) of acetonitrile were added, and MWW-type titanosilicate Catalyst 1 (70 mg) obtained in Example 1 was charged into the flask. The resulting mixture was heated in a water bath at 60° C. under vigorous stirring. Immediately after the temperature of the reaction mixture reached 57° C., 1.1 g (10 mmol as hydrogen peroxide) of 30 mass %-hydrogen peroxide was added to the reaction system. This point was taken as the reaction initiation time, the stirring was continued until 1 hour after the reaction initiation. After 1 hour from the reaction initiation, the reaction mixture was immediately cooled with ice to stop the reaction. Thereafter, the reaction mixture was filtered to separate unreacted diallyl ether, unreacted hydrogen peroxide, water, product and solvent from the catalyst. At this time, the concentration of organic substances in the thus obtained filtrate was analyzed by gas chromatography and the concentration of unreacted hydrogen peroxide was determined by potentiometric titration using Ce(IV). The results of the reaction are shown in the following Table 5. The yield of allyl glycidyl ether as an intended epoxide compound was 24.4%.

TABLE 5

|  | Substrate | Epoxide Product | Yield of Epoxide (%)*1 |
|---|---|---|---|
| Example 14 | diallyl ether | allyl glycidyl ether | 24.4 |
| Example 15 | allyl propyl ether | glycidyl propyl ether | 42.6 |
| Example 16 | allyl chloride | epichlorohydrin | 53.1 |
| Example 17 | styrene | styrene oxide | 1.6 |
| Comparative Example 3 | diallyl ether | allyl glycidyl ether | 16.7 |
| Comparative Example 4 | allyl propyl ether | glycidyl propyl ether | 17.9 |
| Comparative Example 5 | allyl chloride | epichlorohydrin | 20.1 |
| Comparative Example 6 | styrene | styrene oxide | 1.1 |

*1 Yield of epoxide: Amount of epoxide produced (mol)/amount of raw material hydrogen peroxide (mol) × 100 (%)

Example 15

The same operation as in Example 12 was performed except for using 1.00 g (10 mmol) of allyl propyl ether instead of allyl alcohol used in Example 12. The results of the reaction are shown in Table 5 appearing hereinabove. The yield of glycidyl propyl ether as an intended epoxide compound was 42.6%.

Example 16

The same operation as in Example 12 was performed except for using 0.77 g (10 mmol) of allyl chloride instead of allyl alcohol used in Example 12. The results of the reaction are shown in Table 5 appearing hereinabove. The yield of epichlorohydrin as an intended epoxide compound was 53.1%.

Example 17

The same operation as in Example 12 was performed except for using 1.04 g (10 mmol) of styrene instead of allyl alcohol used in Example 12. The results of the reaction are shown in Table 5 appearing hereinabove. The yield of styrene oxide as an intended epoxide compound was 1.6%.

Comparative Examples 3 to 6

The same operation as in Examples 14 to 17 was performed except for using the MFI structure titanosilicate catalyst obtained in Comparative Example 1 instead of the Catalyst 1 obtained in Example 1. The results of the reaction are shown in Table 5 appearing hereinabove. The yield of allyl glycidyl ether was 16.7%, the yield of glycidyl propyl ether was 17.9%, the yield of epichlorohydrin was 20.1%, and the yield of styrene oxide was 1.1%, which were intended epoxide compounds.

Industrial Applicability

As described hereinabove, it is apparent that, as compared with conventionally known titanosilicate catalysts, the crystalline titanosilicate catalyst represented by the following the composition formula (1) or (2) and having a structural code of MWW as described above may function as a very useful catalyst in the production of an oxidized compound from a compound having a carbon-carbon double bond and at least one other functional group by an oxidation reaction using a peroxide as an oxidizing agent:

$$xTiO_2.(1-x)SiO_2 \quad \text{Composition formula (1)}$$

(wherein x is a number of 0.0001 to 0.2).

$$xTiO_2.yM_2O_3.(1-x-2y)SiO_2 \quad \text{Composition formula (2)}$$

(wherein M represents at least one element selected from the group consisting of aluminum, boron, chromium, gallium and iron, x is a number of 0.0001 to 0.2 and y is a number of 0.0001 to 0.1).

It is also clear that according to the process for producing the above-mentioned titanosilicate catalyst using hydrothermal synthesis described above, a high-performance crystalline MWW-type titanosilicate catalyst for providing an oxidized compound can be obtained with good efficiency.

What is claimed is:

1. A process for producing an oxidized compound, comprising: performing an oxidation reaction of a compound having a carbon-carbon double bond and at least one other functional group wherein the carbon-carbon double bond of the compound is oxidized by using a peroxide as an oxidizing agent in the presence of a crystalline MWW-type titanosilicate catalyst for providing an oxidized compound having a MWW structure and being represented by the following composition formula (1):

$$xTiO_2.(1-x)SiO_2$$

wherein x is a number of 0.0001 to 0.2.

2. A process for producing an oxidized compound according to claim 1, wherein the oxidizing agent is at least one compound selected from the group consisting of: hydrogen peroxide, tert-butyl hydroperoxide, tert-amyl hydroperoxide, cumene hydroperoxide, ethylbenzene hydroperoxide, cyclohexyl hydroperoxide, methylcyclohexyl hydroperoxide, tetralin hydroperoxide, isobutylbenzene hydroperoxide, ethylnaphthalene hydroperoxide and peracetic add.

3. A process for producing an oxidized compound according to claim 1, wherein the other functional group in the compound having a carbon-carbon double bond and at least one of other functional group is at least one functional group selected from the group consisting of: an alkenyl group, an alkynyl group, an aryl group, an arene group, an alcohol group, a phenol group, an ether group, an epoxide group, a halogen group, an aldehyde group, a ketone group, a carbonyl group, an ester group, an amide group, a cyanate group, an isocyanate group, a thiocyanate group, an amine group, a diazo group, a nitro group, a nitrile group, a nitroso group, a sulfide group, a sulfoxide group, a sulfone group, a thiol group, an orthoester group, a urea group and an imine group.

4. A process for producing an oxidized compound according to claim 1, wherein the compound having a carbon-carbon double bond and at least one other functional group is at least one compound selected from the group consisting of: allyl ethers, compounds having from 3 to 10 carbon atoms, ethers of polyhydric alcohol, and carboxylic acid esters.

5. A process for producing an oxidized compound according to claim 4, wherein the allyl ether is at least one compound selected from the group consisting of: allyl methyl ether, allyl ethyl ether, allyl propyl ether, allyl butyl ether, allyl vinyl ether and diallyl ether.

6. A process for producing an oxidized compound according to claim 4, wherein the compound having a carbon-carbon double bond and at least one other functional group is diallyl ether or allyl alcohol and the oxidizing agent is hydrogen peroxide.

7. A process for producing an oxidized compound according to claim 4, wherein the compound having from 3 to 10 carbon atoms is at least one compound selected from the group consisting of: allyl alcohol, allyl bromide, an allyl chloride, acrolein, methacrolein and acrylic acid.

8. A process for producing an oxidized compound according to claim 4, wherein the ether of a polyhydric alcohol is at least one compound selected from the group consisting of: ethylene glycol monoalkenyl ether, ethylene glycol dialkenyl ether, 1,2-propanediol monoalkenyl ether, 1,2-propanediol dialkenyl ether, 1,3-propanediol monoalkenyl ether, 1,3-propanediol dialkenyl ether, 1,2-butanediol monoalkenyl ether, 1,2-butanediol dialkenyl ether, 1,3-butanediol monoalkenyl ether, 1,3-butanediol dialkenyl ether, 1,4-butanediol monoalkenyl ether, 1,4-butanediol dialkenyl ether, pentaerythritol monoalkenyl ether, pentaerythritol dialkenyl ether, pentaerythritol trialkenyl ether and pentaerythritol tetraalkenyl ether.

9. A process for producing an oxidized compound according to claim 4, wherein the carboxylic acid ester is at least one compound selected from the group consisting of: allyl formate, allyl acetate, allyl propionate, allyl tartrate, allyl methacrylate, trimethylolpropane monoalkenyl ether, trimethylolpropane dialkenyl ether, and trimethylolpropane trialkenyl ether.

10. A process for producing an oxidized compound according to claim 1, wherein the oxidation reaction is performed in the presence of at least one solvent selected from the group consisting of: alcohols, ketones, nitriles and water.

11. A process for producing an oxidized compound according to claim 1, wherein the oxidized compound is a compound resulting from the epoxidation of the carbon-carbon double bond site of a raw material compound having a carbon-carbon double bond and at least one other functional group, a diol compound resulting from the conversion of the carbon-carbon double bond site of the raw material compound having a carbon-carbon double bond and at least one other functional group, and/or a mixture thereof.

* * * * *